(12) United States Patent
Iwai et al.

(10) Patent No.: US 7,659,419 B2
(45) Date of Patent: Feb. 9, 2010

(54) STABILIZING AGENT FOR HYDROALKOXYSILANE, STABILIZATION METHOD, AND STABILIZED HYDROALKOXYSILANE

(75) Inventors: Makoto Iwai, Ichihara (JP); Stephen P. Ferguson, Midland, MI (US)

(73) Assignees: Dow Corning Corporation, Midland, MI (US); Dow Corning Toray Company, Ltd., Tokyo (JP)

( * ) Notice: Subject to any disclaimer, the term of this patent is extended or adjusted under 35 U.S.C. 154(b) by 45 days.

(21) Appl. No.: 10/566,027

(22) PCT Filed: Jul. 30, 2004

(86) PCT No.: PCT/JP2004/011322

§ 371 (c)(1),
(2), (4) Date: Dec. 1, 2006

(87) PCT Pub. No.: WO2005/010122

PCT Pub. Date: Feb. 3, 2005

(65) Prior Publication Data

US 2007/0093670 A1    Apr. 26, 2007

(30) Foreign Application Priority Data

Jul. 30, 2003    (JP) .............................. 2003-282773

(51) Int. Cl.
*C07F 7/02*    (2006.01)
(52) U.S. Cl. ...................................... 556/482; 556/470
(58) Field of Classification Search ................. 556/482, 556/470
See application file for complete search history.

(56) References Cited

U.S. PATENT DOCUMENTS 2,364,410 A    12/1944    Whittaker
4,113,751 A    9/1978     Arnold
5,693,839 A    12/1997    Reitmeier et al.

FOREIGN PATENT DOCUMENTS

| JP | 55072198  | 5/1980  |
| JP | 63313790  | 12/1988 |
| JP | 1090192   | 4/1989  |
| JP | 3244666   | 10/1991 |
| JP | 6220417   | 8/1994  |
| JP | 9077779   | 3/1997  |
| JP | 10072209  | 3/1998  |

OTHER PUBLICATIONS

English language abstract for JP3244666 obtained from espacenet.com, Nov. 28, 2006.
English language abstract for JP6220417 obtained from espacenet.com, Aug. 9, 2006.
English language abstract for JP9077779 obtained from espacenet.com, Nov. 28, 2006.
English language abstract for JP10072209 obtained from espacenet.com, Nov. 28, 2006.
English language abstract for JP1090192 obtained from espacenet.com, Nov. 28, 2006.
English language abstract for JP55072198 obtained from espacenet.com, Nov. 28, 2006.
English language abstract for JP63313790 obtained from espacenet.com, Aug. 9, 2006.

*Primary Examiner*—Elvis O Price
(74) *Attorney, Agent, or Firm*—Howard & Howard Attorneys PLLC

(57) ABSTRACT

A stabilizing agent for a hydroalkoxysilane such as triethoxysilane and trimethoxysilane characterized by comprising a carboxylate such as an alkali metal salt or an alkali earth metal salt of a carboxylic acid having 1 to 18 carbon atoms; a method for stabilizing a hydroalkoxysilane by combining it with a carboxylate; and a hydroalkoxysilane stabilized with a carboxylate.

28 Claims, No Drawings

STABILIZING AGENT FOR HYDROALKOXYSILANE, STABILIZATION METHOD, AND STABILIZED HYDROALKOXYSILANE

RELATED APPLICATIONS

This application claims priority to and all the advantages of International Application No. PCT/JP2004/011322, filed on Jul. 30, 2004, which claims priority to Japanese Patent Application No. 2003-282773, filed on Jul. 30, 2003.

TECHNICAL FIELD

The present invention relates to a stabilizing agent for a hydroalkoxysilane during storage or transportation thereof, as well as to a method for stabilizing a hydroalkoxysilane and to a hydroalkoxysilane stabilized with the aforementioned stabilizing agent.

BACKGROUND ART

Hydroalkoxysilanes are industrially important compounds as intermediates used in manufacturing various organosilicon compounds and silicon-functional polymers. Since they contain at least one silicon-bonded hydrogen atoms as well as at least one silicon-bonded alkoxy groups in the molecule, they possess high reactivity and require a great deal of attention during storage and transportation. Normally, hydroalkoxysilanes are highly volatile and should be kept in sealed containers. The problem associated with their storage is that under the effect of the reaction described below, a hydroalkoxysilane either loose purity, undergo chemical changes, or develop an increased pressure in a storage container.

1) A dihydroalkoxysilane represented by the general formula: $H_2Si(OR)_2$ wherein R is alkyl group that is a low-boiling-point compound resulting from a disproportionation reaction is formed in accordance with the following scheme:

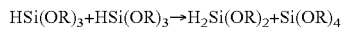

2) Gaseous hydrogen is generated under the effect of a dehydration reaction with participation of hydrochloric acid, an alcohol, or moisture.

Various attempts have been made to solve the above problems. For example, Japanese Unexamined Patent Application Publication (hereinafter referred to as Kokai) S55-72198 discloses a method based on coexistence of a hydroalkoxysilane with an organophosphorous compound, while Kokai S63-313790 is based on the use of an organic halide. Kokai H1-90192 exemplifies methods where a hydroalkoxysilane is combined with an inorganic acid or a Lewis acid. However, all these methods still could not provide sufficient stability to the hydroalkoxysilane.

It was proposed in Kokai H6-220417 to use an epoxide, and in Kokai H10-72209 it was reported that admixing a hydroalkoxysilane with a hydrocarbon optionally having a functional group selected from the group consisting of among carboxylic ester, aldehyde, keto, ether, thioether, tertiary amino, epoxy and cyano groups and halogen atoms is effective for stabilization. Furthermore, Kokai H9-77779 discloses a purification method for a hydroalkoxysilane by admixing it with methyl formate. However, since these organic compounds are soluble in hydroalkoxysilanes, the aforementioned method requires subsequent removal operations.

SUMMARY OF THE INVENTION

As a result of extensive studies aimed at finding an improved stabilizing agent for a hydroalkoxysilane, a improved stabilization method, and a stabilized hydroalkoxysilane which are free of the aforementioned drawbacks, the inventors have revealed that a hydroalkoxysilane can be efficiently stabilized with a carboxylate, and that coexistence of a hydroalkoxysilane with a carboxylate can eliminate such problems as loss of purity and chemical changes during storage and transportation, and a pressure rise in a storage container. Such coexistence provides a stabilized hydroalkoxysilane and facilitates separation and removal of the stabilizing agent from the stabilized hydroalkoxysilane after storage and transportation. Thus the inventors arrived at the present invention. In view of the above, it is an object of the present invention to provide an improved stabilizing agent and an improved method that stabilizes a hydroalkoxysilane, provide a hydroalkoxysilane with improved stability, and facilitate separation and removal of the stabilizing agent after storage and transportation of the stabilized hydroalkoxysilane are completed.

Namely, the present invention relates to the following:

[1] A stabilizing agent for a hydroalkoxysilane characterized by comprising a carboxylate.

[2] The stabilizing agent according to [1], wherein said carboxylate is an alkali metal salt or an alkali earth metal salt of a carboxylic acid having 1 to 18 carbon atoms.

[3] The stabilizing agent according to [2], wherein said carboxylate is an alkali metal salt or an alkali earth metal salt of a carboxylic acid having 1 to 5 carbon atoms.

[4] The stabilizing agent according to [3], wherein said alkali metal salt or alkali earth metal salt of a carboxylic acid having 1 to 5 carbon atoms are selected from the group consisting of sodium formate, sodium acetate, sodium propionate, sodium butyrate, sodium valerate or pentanoate, sodium oxalate, potassium formate, potassium acetate, magnesium acetate, and calcium acetate.

[5] A method for stabilizing a hydroalkoxysilane characterized by the fact that said hydroalkoxysilane coexists with a carboxylate.

[6]. The method according to [5], wherein said carboxylate is an alkali metal salt or an alkali earth metal salt of a carboxylic acid having 1 to 18 carbon atoms.

[7] The method according to [6], wherein said carboxylate is an alkali metal salt or an alkali earth metal salt of a carboxylic acid having 1 to 5 carbon atoms.

[8] The method according to [7], wherein said alkali metal salt or alkali earth metal salt of a carboxylic acid having 1 to 5 carbon atoms are selected from the group consisting of sodium formate, sodium acetate, sodium propionate, sodium butyrate, sodium valerate or pentanoate, sodium oxalate, potassium formate, potassium acetate, magnesium acetate, and calcium acetate.

[9] The method according to [5], wherein said carboxylate coexists with said hydroalkoxysilane in an amount of 0.0001 to 10 parts by weight per 100 parts by weight of said hydroalkoxysilane.

[10] The method according to [5], wherein said hydroalkoxysilane is a trialkoxysilane.

[11] The method according to [10], wherein said trialkoxysilane is trimethoxysilane or triethoxysilane.

[12] The method according to [5], wherein said hydroalkoxysilane is an alkyldialkoxysilane.

[13] The method according to [12], wherein said alkyldialkoxysilane is a methyldimethoxysilane or methyldiethoxysilane.

[14] A hydroalkoxysilane characterized by being stabilized with a carboxylate.

[15] The hydroalkoxysilane according to [14], wherein said carboxylate is an alkali metal salt or an alkali earth metal salt of a carboxylic acid having 1 to 18 carbon atoms.

[16] The hydroalkoxysilane according to [14], wherein said carboxylate is an alkali metal salt or an alkali earth metal salt of a carboxylic acid having 1 to 5 carbon atoms

[17]. The hydroalkoxysilane according to [16], wherein said alkali metal salt or alkali earth metal salt of a carboxylic acid having 1 to 5 carbon atoms are selected from the group consisting of sodium formate, sodium acetate, sodium propionate, sodium butyrate, sodium valerate or pentanoate, sodium oxalate, potassium formate, potassium acetate, magnesium acetate, and calcium acetate.

A stabilizing agent of the present invention can protect a hydroalkoxysilane from the loss of purity and chemical changes during storage and transportation, prevent a pressure rise in a container where the hydroalkoxysilane is stored, and facilitate separation of a stabilizing agent from the stabilized hydroalkoxysilane by filtering or centrifugation when the hydroalkoxysilanes is used as a reactant, a reaction starting material, or an additive and when it is required to obtain a product or a composition free of any stabilizing agent residue.

A stabilization method of the present invention can prevent a hydroalkoxysilane from the loss of purity and chemical changes during storage and transportation, prevent a pressure rise in a container where the hydroalkoxysilane is stored, and facilitate separation of a stabilizing agent from the stabilized hydroalkoxysilane by filtering or centrifugation when the hydroalkoxysilane is used as a reactant, a reaction starting material, or an additive and when it is required to obtain a product or a composition free of any stabilizing agent residue.

A stabilized hydroalkoxysilane of the present invention is not subject to loss of purity and chemical changes during storage and transportation, and a pressure rise in a container where the hydroalkoxysilane is stored, and facilitate separation of a stabilizing agent from the stabilized hydroalkoxysilane by filtering or centrifugation when the hydroalkoxysilane is used as a reactant, a reaction starting material, or an additive and when it is required to obtain a product or a composition free of any stabilizing agent residue.

BEST MODE FOR CARRYING OUT THE INVENTION

A carboxylate coexisting with a hydroalkoxysilane protects the hydroalkoxysilane from loss of purity and chemical changes, and prevents a pressure rise in a storage container where the hydroalkoxysilane is stored. Furthermore, since the carboxylate is not soluble in the hydroalkoxysilane, if necessary, it can be easily separated from the hydroalkoxysilane by filtering or centrifugation and thus removed. Thus, one should not be concerned that the carboxylate may remain in, or be admixed with, the hydroalkoxysilane as an impurity.

The aforementioned carboxylate can be represented by an alkali metal salt or alkali earth metal salt of a carboxylic acid. A preferable carboxylic acid is a monocarboxylic acid, but it can also be represented by a dicarboxylic acid, tricarboxylic acid, or a similar polycarboxylic acid. The aforementioned carboxylic acids may contain 1 to 18 carbon atoms, preferably 1 to 10 carbon atoms, and even more preferably 1 to 5 carbon atoms. If the number of carbon atoms exceeds the upper recommended limit, this will increase the molecular weight, and reduce the share of the carboxylic acid component relative to the addition amount, and therefore will require the use of the carboxylate in a larger quantity. An alkali metal may comprise sodium or potassium, and an alkali earth metal can be represented by magnesium and calcium.

The following are examples of carboxylic acids suitable for the purposes of the present invention: sodium formate, sodium acetate, sodium propionate, sodium butyrate, sodium valerate or sodium pentanoate, sodium oxalate, potassium formate, potassium acetate, magnesium acetate, and calcium acetate. Sodium acetate is most preferable since it is easily obtainable and easy to handle. Regarding the carboxylate, an anhydride is preferable since it does not cause hydrolysis of the hydroalkoxysilane, and the form of powder or granule at room temperature is preferable since it can be easily filtered. There are no special restrictions with regard to the size of the powder or granule, but in general its size may be within the range of 1 to 1000 μm.

It is recommended for a carboxylate to coexist with a hydroalkoxysilane in an amount of 0.0001 to 10 parts by weight, preferably 0.001 to 5 parts by weight, and even more preferably 0.01 to 3 parts by weight per 100 parts by weight of the hydroalkoxysilane. If the carboxylate is used in an amount less than the lower recommended limit, it may be difficult to provide the hydroalkoxysilane with sufficient stability. If, on the other hand, the carboxylate is used in an amount exceeding the upper recommended limit, it may impair workability for separating and removing the carboxylate.

The hydroalkoxysilane has at least one silicon-bonded hydrogen atoms and at least one silicon-bonded alkoxy groups in one molecule. It is preferably represented by the following general formula (1):

$$H(R^1)_x Si(OR^2)_{3-x} \quad (1)$$

In this formula, $R^1$ is a univalent hydrocarbon group that is exemplified by methyl group, ethyl group, propyl group, isopropyl group, butyl group, cyclohexyl group, or a similar alkyl group; a vinyl group, allyl group, butenyl group, hexenyl group, or a similar alkenyl group; phenyl group, tolyl group, xylyl group, or a similar aryl group. Of these, most preferable is an alkyl group with 1 to 18 carbon atoms, preferably 1 to 6 carbon atoms; $R^2$ is an alkyl group with 1 to 5 carbon atoms, and "x" is 0, 1, or 2.

The following are representative examples of hydroalkoxysilanes suitable for the purposes of the present invention: a hydrotrialkoxysilane (i.e., trialkoxysilane), hydroalkyldialkoxysilane (i.e., alkyldialkoxysilane), and hydrodialkylalkoxysilane (i.e., dialkylalkoxysilane). The trialkoxysilane can be represented by trimethoxysilane, triethoxysilane, tri-(n-propoxy) silane, and tri-(iso-propoxy) silane. The alkyldialkoxysilane can be represented by methyldimethoxysilane, methyldiethoxysilane, methyldi-(iso-propoxy) silane, ethyldimethoxysilane, ethyldiethoxysilane, n-butyldimethoxysilane, tert-butyldimethoxysilane, and cyclohexyldimethoxysilane. A dialkylalkoxysilane can be represented by dimethylmethoxysilane and dimethylethoxysilane.

A carboxylate can be combined with the aforementioned hydroalkoxysilane by adding the carboxlane to the hydroalkoxysilane and stirring, mixing, or shaking. The stabilized hydroalkoxysilane in accordance with the present invention can be easily produced by adding the carboxylate to the hydroalkoxysilane and then subjecting them to stirring, mixing, or shaking. In order to prevent vaporization of the hydroalkoxysilane and contact with moisture of air, it is recommended to store the stabilized hydroalkoxysilane in a sealed container. Coexistence of the hydroalkoxysilane with the aforementioned stabilizing agent protects the hydroalkoxysilane from the loss of purity and chemical changes during storage and transportation, and prevents a pressure rise in a storage container. As a result, it becomes possible to prolong the storage time and to provide safety during transportation. When the stabilized hydroalkoxysilane is used as a reagent, a starting material, or as an additive, the stabilizing agent can be easily separated by filtering or centrifugation and then removed, so that the product or composition will be free of any stabilizing agent residue.

EXAMPLES

In the subsequent examples and comparative examples, GC % designates percentage determined from the specific surface area on a gas-chromatography chart.

Example 1

A 20 mL glass test tube was filled with a 10 g of triethoxysilane and 0.01 g of powdered anhydrous sodium acetate (a commercially produced special-class reagent). The test tube was sealed and held at 25° C. Thirty days later, purity of triethoxysilane contained in the test tube and the amount of generated tetraethoxysilane were measured by means of gas chromatography. The results of measurements are shown in Table 1. After the test tube with the 30-day stored content was well shaken, the mixture of the aforementioned 10 g of triethoxysilane and 0.01 g of powdered anhydrous sodium acetate was almost instantly filtered through a membrane filter (a polytetrafluoroethylene filter having a 0.45 μm diameter perforations; the product of Millipore Corporation; trademark "Millex-FH") fit onto the tip of the 20 mL glass syringe. As a result, the entire content of the powdered sodium acetate was filtered out.

Example 2 and Example 3

The process was conducted in the same manner as in Example 1, with the exception that powdered anhydrous sodium formate (a commercially produced special-class reagent) and powdered anhydrous potassium acetate (a commercially produced special-class reagent) were used instead of the aforementioned powdered sodium acetate. The results of measurements after the storage are shown in Table 1. Furthermore, after 30-day storage under the same conditions as in Example 1, the product was almost instantly filtered through a membrane filter. As a result, the entire content of the powdered sodium formate and powdered potassium acetate was filtered out.

Comparative Example 1

The process was conducted in the same manner as in Example 1, with the exception that liquid methyl formate was used instead of the aforementioned powdered sodium acetate. The product was stored and measured as in Example 1. After storage, however, the methyl formate was found dissolved in triethoxysilane and removal thereof required an additional operation, such as distillation.

Comparative Example 2

10 g of triethoxysilane were loaded into a 20 mL glass sample tube without addition of any stabilizing agent, such as the powdered sodium acetate. The test tube was sealed, and the content was stored at 25° C. Thirty days later, purity of the triethoxysilane and a produced amount of the tetraethoxysilane were measured with the use of gas chromatography. The results of measurements are shown in Table 1.

TABLE 1

|  | Stabilizing agent | Triethoxysilane (GC %) | Tetraethoxysilane (GC %) |
|---|---|---|---|
| Example 1 | Sodium acetate | 99.9 | 0.1 |
| Example 2 | Sodium acetate | 99.9 | 0.1 |
| Example 3 | Potassium acetate | 99.9 | 0.1 |
| Comparative Example 1 | Methyl formate | 99.7 | 0.2 |
| Comparative Example 2 | None | 96.3 | 3.5 |

Example 4, Example 5 and Example 6

The process was conducted and the product was stored in the same manner as in Example 1, Example 2 and Example 3, except that methyldimethoxysilane was used instead of triethoxysilane. After 30-day storage, the residual amount of the methyldimethoxysilane and the produced amount of methyltrimethoxysilane contained in the test tube were measured by gas chromatography. The results are shown in Table 2.

Comparative Example 3

The process was conducted and the product was stored in the same manner as in Example 1, with the exception that liquid methylglycidyl ether was used instead of the powdered sodium acetate. The results are shown in Table 1. After storage, however, the methylglycidyl ether was found dissolved in triethoxysilane and removal thereof required additional operations of filtering and distillation.

Comparative Example 4

10 g of methyldimethoxysilane were loaded into a 20 mL glass-made sample tube without addition of any stabilizing agent, such as the powdered sodium acetate. The test tube was sealed, and the content was stored at 25° C. Thirty days later, a residual amount of the methyldimethoxysilane and a produced amount of the methyltrimethoxysilane contained in the test tube were measured with the use of gas chromatography. The results of measurements are shown in Table 2.

TABLE 2

| | Stabilizing agent | Methyldimethoxysilane (GC %) | Methyltrimethoxysilane (GC %) |
|---|---|---|---|
| Example 4 | Sodium acetate | 99.9 | 0.1 |
| Example 5 | Potassium acetate | 99.8 | 0.1 |
| Example 6 | Potassium acetate | 99.9 | 0.1 |
| Comparative Example 3 | Methylglycidyl ether | 99.7 | 0.1 |
| Comparative Example 4 | None | 99.3 | 3.6 |

Example 7

A 100 mL glass flask with a drain valve was filled with 20 g of methyldimethoxysilane and 0.02 g of powdered anhydrous sodium acetate (a commercially produced reagent of a special class). The flask was sealed, and the content heated for 3 days in an oil bath at 50° C. Upon completion of heating, the flask was cooled to room temperature, the drain valve was opened, the amount of the generated gas was measured, and it was confirmed that pressure developed inside the flask. Purity of the methyldimethoxysilane and the amount of the formed methyltrimethoxysilane were measured by gas chromatography. The results are shown in Table 3. After 3-day heating, a mixture composed of 20 g of methyldimethoxysilane and 0.02 g of powdered sodium acetate was filtered in the same manner as in Example 1 with almost instant separation of the entire powdered sodium acetate.

Comparative Example 5

The test was carried out in a methyldimethoxysilane under the same conditions as in Example 7, with the exception that the powdered sodium acetate was not used. The results are shown in Table 3.

TABLE 3

| | Stabilizing agent | Amount of generated gas (mL) | Methyldimethoxysilane (GC %) | Methyltrimethoxysilane (GC %) |
|---|---|---|---|---|
| Example 7 | Sodium acetate | Less than 0.1 | 99.9 | 0.1 |
| Comparative Example 5 | None | 4.8 | 95.0 | 4.8 |

INDUSTRIAL APPLICABILITY

The stabilizing agent and the stabilization method of the present invention are useful for protecting a hydroalkoxysilane from the loss of purity and chemical changes during storage and transportation, and preventing a pressure rise in a storage container. A stabilized hydroalkoxysilane of the present invention is very useful in various industries since it does not loose its purity, is not subject to chemical changes during transportation and storage, and prevents a pressure rise in a storage container.

The invention claimed is:

1. A method for producing a stabilized hydroalkoxysilane, said method comprising the steps of:
   providing a hydroalkoxysilane;
   providing a carboxylate;
   combining the carboxylate with the hydroalkoxysilane in the absence of any epoxide in a container to form the stabilized hydroalkoxysilane;
   sealing the container to form a sealed container containing the stabilized hydroalkoxysilane; and
   separating the carboxylate from the hydroalkoxysilane.

2. The method according to claim 1, wherein the carboxylate is an alkali metal salt or an alkali earth metal salt of a carboxylic acid having 1 to 18 carbon atoms.

3. The method according to claim 2, wherein the alkali metal salt or alkali earth metal salt of a carboxylic acid has 1 to 5 carbon atoms.

4. The method according to claim 3, wherein the alkali metal salt or alkali earth metal salt of a carboxylic acid having 1 to 5 carbon atoms is selected from the group consisting of sodium formate, sodium acetate, sodium propionate, sodium butyrate, sodium valerate or pentanoate, sodium oxalate, potassium formate, potassium acetate, magnesium acetate, and calcium acetate.

5. The method according to claim 1, wherein the carboxylate coexists with the hydroalkoxysilane in an amount of 0.0001 to 10 parts by weight per 100 parts by weight of the hydroalkoxysilane prior to separation.

6. The method according to claim 1, wherein the hydroalkoxysilane is a trialkoxysilane.

7. The method according to claim 6, wherein the trialkoxysilane is a trimethoxysilane or a triethoxysilane.

8. The method according to claim 1, wherein the hydroalkoxysilane is an alkyldialkoxysilane.

9. The method according to claim 8, wherein the alkyldialkoxysilane is a methyldimethoxysilane or a methyldiethoxysilane.

10. A stabilized hydroalkoxysilane comprising a combination of a hydroalkoxysilane and a carboxylate in the absence of any epoxide, wherein said stabilized hydroalkoxysilane is stored and transported in a sealed container and wherein said carboxylate is separated from said stabilized hydroalkoxysilane prior to use of said hydroalkoxysilane as a reagent, starting material, or additive.

11. The stabilized hydroalkoxysilane according to claim 10, wherein said carboxylate is an alkali metal salt or an alkali earth metal salt of a carboxylic acid having 1 to 18 carbon atoms.

12. The stabilized hydroalkoxysilane according to claim 11, wherein said alkali metal salt or alkali earth metal salt of a carboxylic acid has 1 to 5 carbon atoms.

13. The stabilized hydroalkoxysilane according to claim 12, wherein said alkali metal salt or alkali earth metal salt of a carboxylic acid having 1 to 5 carbon atoms is selected from the group consisting of sodium formate, sodium acetate, sodium propionate, sodium butyrate, sodium valerate or pentanoate, sodium oxalate, potassium formate, potassium acetate, magnesium acetate, and calcium acetate.

14. The method according to claim 1, wherein said step of combining the carboxylate with the hydroalkoxysilane in the container to form the stabilized hydroalkoxysilane is further defined as adding the carboxylate to the hydroalkoxysilane.

15. The method according to claim 1 further comprising the step of mixing the stabilized hydroalkoxysilane.

16. The method according to claim 1 further comprising the steps of storing and transporting the sealed container.

17. The method according to claim 16, wherein the stabilized hydroalkoxysilane is stored and transported in the sealed container without a loss of purity and chemical changes.

18. The method according to claim 16, wherein the stabilized hydroalkoxysilane is stored and transported in the sealed container without a pressure rise in the sealed container.

19. The method according to claim 1, wherein the carboxylate is separated from the hydroalkoxysilane through filtration.

20. The stabilized hydroalkoxysilane according to claim 10 wherein said carboxylate is separated from said hydroalkoxysilane through filtration.

21. A method for producing a stabilized hydroalkoxysilane, said method comprising the steps of:
providing a hydroalkoxysilane;
providing a carboxylate;
adding the carboxylate to the hydroalkoxysilane in the absence of any epoxide in a container to form the stabilized hydroalkoxysilane;
mixing the stabilized hydroalkoxysilane in the absence of any epoxide;
sealing the container to form a sealed container containing the stabilized hydroalkoxysilane; and
separating the carboxylate from the hydroalkoxysilane.

22. The method according to claim 21, wherein said step of mixing is further defined as stirring and/or shaking the stabilized hydroalkoxysilane.

23. The method according to claim 21 further comprising the steps of storing and transporting the sealed container.

24. The method according to claim 1 wherein the carboxylate is in powdered or granulated form.

25. The method according to claim 1 wherein the carboxylate is separated from the hydroalkoxysilane in the absence of any epoxides.

26. The stabilized hydroalkoxysilane according to claim 10 wherein the carboxylate is in powdered or granulated form.

27. The method according to claim 21 wherein the carboxylate is in powdered or granulated form.

28. The method according to claim 21 wherein the carboxylate is separated from the hydroalkoxysilane in the absence of any epoxides.

* * * * *